United States Patent
Furusho

(10) Patent No.: US 10,640,772 B2
(45) Date of Patent: May 5, 2020

(54) DNA APTAMERS BINDING TO MOLECULAR TARGETED AGENTS AND DETECTION METHOD OF MOLECULAR TARGETED MEDICINE USING THE SAME

(71) Applicant: NISSAN CHEMICAL INDUSTRIES, LTD., Tokyo (JP)

(72) Inventor: Hitoshi Furusho, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/779,753

(22) PCT Filed: Nov. 29, 2016

(86) PCT No.: PCT/JP2016/085440
§ 371 (c)(1),
(2) Date: May 29, 2018

(87) PCT Pub. No.: WO2017/094733
PCT Pub. Date: Jun. 8, 2017

(65) Prior Publication Data
US 2019/0284560 A1    Sep. 19, 2019

(30) Foreign Application Priority Data

Nov. 30, 2015 (JP) .................. 2015-233842
Dec. 9, 2015 (JP) .................. 2015-240517

(51) Int. Cl.
| | |
|---|---|
| A61K 48/00 | (2006.01) |
| C07H 21/04 | (2006.01) |
| C12N 15/115 | (2010.01) |
| B82Y 5/00 | (2011.01) |
| B82Y 15/00 | (2011.01) |
| B82Y 25/00 | (2011.01) |
| C07K 16/22 | (2006.01) |
| G01N 33/52 | (2006.01) |
| G01N 33/577 | (2006.01) |
| G01N 33/53 | (2006.01) |
| G01N 33/50 | (2006.01) |

(52) U.S. Cl.
CPC .............. *C12N 15/115* (2013.01); *B82Y 5/00* (2013.01); *B82Y 15/00* (2013.01); *B82Y 25/00* (2013.01); *C07K 16/22* (2013.01); *G01N 33/50* (2013.01); *G01N 33/52* (2013.01); *G01N 33/53* (2013.01); *G01N 33/577* (2013.01); *C07K 2317/24* (2013.01); *C07K 2317/41* (2013.01)

(58) Field of Classification Search
CPC ........................ A61K 45/06; A61K 31/713
See application file for complete search history.

(56) References Cited

U.S. PATENT DOCUMENTS

| | | | |
|---|---|---|---|
| 8,883,832 B2 * | 11/2014 | Shalwitz .............. | C07D 277/28 514/254.02 |
| 2010/0055706 A1 | 3/2010 | Greinacher et al. | |
| 2011/0076279 A1 | 3/2011 | Ramachandra et al. | |
| 2016/0106858 A1 * | 4/2016 | Hall ...................... | C07K 16/18 424/450 |
| 2016/0176935 A1 * | 6/2016 | Libutti .................. | C07K 14/47 514/44 R |

FOREIGN PATENT DOCUMENTS

| | | |
|---|---|---|
| JP | 2010-507594 A | 3/2010 |
| JP | 2012-501631 A | 1/2012 |
| JP | 2013-40118 A | 2/2013 |
| JP | 2014-217311 A | 11/2014 |
| JP | 2015-62423 A | 4/2015 |
| JP | 2016-21883 A | 2/2016 |
| WO | WO 91/19813 A1 | 12/1991 |

OTHER PUBLICATIONS

Lee et al. (Current Topics in Medicinal Chemistry, 2013, 13, 504-512).*
Hong et al. (Curr Med Chem. Sep. 1, 2011; 18(27): 4195-4205).*
English translation of International Preliminary Report on Patentability and Written Opinion dated Jun. 14, 2018, in PCT/JP2016/085440 (Forms PCT/IB/326, PCT/IB/373, PCT/ISA/237).
English translation of International Search Report dated Jan. 17, 2018, in PCT/JP2016/085440.
Guo et al., "CELL-SELEX: Novel Perspectives of Aptamer-Based Therapeutics," Int. J. Mol. Sci. (2008), vol. 9, pp. 668-678.
Jiang et al., "Signaling Aptamer/Protein Binding by a Molecular Light Switch Complex," Anal. Chem. (2004), vol. 76, pp. 5230-5235.
Shieh et al., "Aptamer-Based Tumor-Targeted Drug Delivery for Photodynamic Therapy," ACS NANO (2010), vol. 4, No. 3, pp. 1433-1442.
Extended European Search Report dated Apr. 29, 2019, in European Patent Application No. 16870670.3.
Missailidis et al., "Selection of aptamers with high affinity and high specificity against C595, an anti-MUC1 IgG3 monoclonal antibody, for antibody targeting," Journal of Immunological Methods (2005), vol. 296, pp. 45-62.

(Continued)

*Primary Examiner* — Amy H Bowman
(74) *Attorney, Agent, or Firm* — Birch, Stewart, Kolasch & Birch, LLP

(57) ABSTRACT

The objective of the present invention is to provide a DNA aptamer that can specifically binding to a molecular targeted medicine, a composition comprising the DNA aptamer, and a method for detecting a molecular targeted medicine using the DNA aptamer.
A DNA aptamer comprising specifically binding to a molecular targeted medicine, a composition for detecting a molecular targeted medicine comprising the DNA aptamer, a kid for detecting a molecular targeted medicine, and a method for detecting a molecular targeted medicine comprising using the DNA aptamer.

12 Claims, 2 Drawing Sheets

Specification includes a Sequence Listing.

(56) References Cited

OTHER PUBLICATIONS

Wang et al., "Anti-MUC1 Monoclonal Antibody (C595) and Docetaxel Markedly Reduce Tumor Burden and Ascites, and Prolong Survival in an in vivo Ovarian Cancer Model," PLoS One (Sep. 2011), vol. 6, No. 9, e24405, pp. 1-13.

Yamada et al., "Anti-Idiotype DNA Aptamer Affinity Purification-High-Temperature Reversed-Phase Liquid Chromatography: A Simple, Accurate, and Selective Bioanalysis of Bevacizumab," Molecules (2019), vol. 24, No. 857, pp. 1-12.

Yamada et al., "High-Throughput Bioanalysis of Bevacizumab in Human Plasma Based on Enzyme-Linked Aptamer Assay Using Anti-Idiotype DNA Aptamer," Anal. Chem. (2019), vol. 91, pp. 3125-3130.

* cited by examiner

FIGURE:
Making of the double-stranded DNA into a single strand using magnetic particles

DNA APTAMERS BINDING TO MOLECULAR TARGETED AGENTS AND DETECTION METHOD OF MOLECULAR TARGETED MEDICINE USING THE SAME

TECHNICAL FIELD

The objective of the present invention is to provide DNA aptamers that can specifically bind to molecular targeted medicines, compositions comprising the DNA aptamers, and methods for detecting a molecular targeted medicine using the DNA aptamer.

BACKGROUND ART

Cancer still accounts for a large percentage of death cause deriving from diseases and many molecular targeted medicines for cancer treatment are developed. The effect of the use of such anti-cancer agent used in the treatment may be increased by measuring the blood concentration of anti-cancer agent at diagnosis. As such, knowing the blood retention state of a drug is the most important objective in the interdisciplinary studies including medicine and biology.

Proteins have a specific conformational structure and the structure renders the specificity. In particular, the conformational structure of the Fab part of the antibody protein is an essential structure of the detection of a specific antigen in the biological body and plays a role in the antibody reaction. In the recent years, the development of molecular targeted medicines with the focus on the specific recognition ability of these antibody proteins have progressed rapidly and has dramatically improved the 5 years survival rate in cancer patients. For example, bevacizumab which is one of the antibody molecular targeted medicines that is sold under the product name of Avastin has a feature of reducing the proliferation speed of cancer by inhibiting angiogenesis. Because cancer cells actively perform cell proliferation as compared to normal cells in general, they require more nutrients and oxygen than normal cells, and thus, form blood vessels around the cancer tissues. As for angiogenesis, vascular endothelial cell growth factor (VEGF) is required and bevacizumab has an effect to inhibit this vascular endothelial cell growth factor. As such, bevacizumab inhibits angiogenesis around the cancer cells, and by blocking the nutrients provided to the cancer cells, it inhibits the proliferation of cancer cells. Accordingly, bevacizumab has no toxicity on cancer cells, has an advantage that it could be combinedly used with other anti-cancer agents, and thus, it is widely used as cancer therapeutic drugs. Therefore, bevacizumab is used for the treatment of colon cancer, rectal cancer, non-small-cell lung cancer, ovarian cancer, and breast cancer (for example, Non-Patent Documents 1 and 2).

For the measurement of blood bevacizumab concentration in the treatment, immune antibody method is used; however, this method has a drawback in that the operation is very complicated as well as that the test kit is expensive, and thus, it cannot be carried out frequently.

Because a single-stranded nucleic acid takes various conformational structures depending on its base sequence, a base structure having an affinity to a specific antigen can be found. Nucleic acids specifically adsorbing to these targets of purpose are called aptamers. For the screening of a novel aptamer, in vitro selection method is used as the most effective means. In particular, Systematic Evolution of Ligands by Exponential enrichment (SELEX) method is roughly divided into two steps: the selection of target nucleic acid molecules and the amplification of selected aptamers (for example, Patent Document 1). Repetition of the selection and amplification of the target nucleic acid molecule while increasing selectivity results in the obtainment of nucleic acid fragments with high affinity. Moreover, in the recent years, various improvements have been made, and reports are made on such as methods with superior efficiency and selectiveness which can collect aptamers with lesser number of cycles and methods obtaining aptamers binding not only to low molecules and proteins but also to cells and tissues (more precisely, to the molecules present on the surface) (Cell-SELEX method; for example, Non-Patent Document 3). In comparison to the conventional SELEX method, this method features the following: Analysis of proteins is unnecessary, various membrane protein aptamers present on the cell surface could be simultaneously selected, and furthermore, aptamers that further specifically bind to target cells could be selected. These aptamers have advantages that cannot be found in antibodies such as the following: synthesis can be performed chemically and in a short period of time, the modification of molecules can be performed economically, the action mechanism is simple, and hardly any immunogenicity is reported, which are additional advantages other than the high-affinity and specificity to a target that is featured by an antibody conventionally used in diagnosis and treatment.

Searching for a nucleic acid sequence having an affinity to an antibody protein, for example, other than to cells, can be easily carried out by using Protein A beads (Manufactured by Thermo Scientific Inc.) magnetic particles. When the aptamers having an affinity to the discovered antibody is used for diagnosis and examination, fluorescent dyes are introduced to the terminus, and detection under the fluorescence microscope is performed in most cases (for example, Non-Patent Document 2).

In medical oncology treatment, the combined use of anti-cancer agents can be effective. Here, two-agent combination therapy of those apart from molecular targeted medicines has demonstrated excellent results as compared to the conventional treatments; however, any combination showed equivalent results and the treatment results leveled off. On the other hand, antibody drugs such as molecular targeted medicines have presented a breakthrough achievement. The first report of molecular targeted medicine in Japan is IRESSA (Gefitinib). Although cases showing a dramatic therapeutic results using IRESSA (Gefitinib) are reported, no statistical effect has been shown. Nonetheless, it was believed to have a relative high effect in non-smokers and adenocarcinoma cancer patients. In 2009, Alimta was approved, and the combined used of this with cisplatin was shown to extend the survival rate of non-small-cell lung cancer except squamous cell carcinoma. Bevacizumab, which was approved subsequently, is referred to as an angiogenesis inhibitor, and by supplementing a vascular endothelial cell growth factor, angiogenesis is suppressed, the provision of nutrients to cancer cells is suppressed, and thereby cancer proliferation can be suppressed. Bevacizumab does not have toxicity on cancer cell itself, and thus, it is used in combination with other anti-cancer agents, e.g., the combined use with Carboplatin and Paclitaxel extended the overall survival period for 14.2 months.

As such, at present, antibody drug is a most commonly used molecular targeted medicine for cancer treatment. Moreover, antibody drugs suitable for the treatment of diseases such as Rheumatoid arthritis, Crohn's disease, and Asthma in addition to cancer are developed. Furthermore, these antibody drugs could cause problems such as side effects caused by excessive administration as in low molecular drugs and the measurement of blood concentration of antibody drug is difficult as compared to that of the low molecular drug. For this reason, at present, a simple measurement technique of blood concentration of a molecular targeted medicine is demanded to further improve the therapeutic effect.

PRIOR ART DOCUMENTS

Patent Documents

Patent Document 1: WO/9119813

Non-Patent Documents

Non-Patent Document 1: Yawl Jiang, Xiahong Fang, and Chunli Bai., Anal chem., 76(17): 5230-3235, 2004.
Non-Patent Document 2: Yen-An Shieh, Shu-Jyuan Yang, Ming-Feng Wei and Ming-JiumShieh., ACS NANO., Vol. 4, No. 3, 1433-1442, 2010.
Non-Patent Document 3: Guo, et al., Int. J. Mol. Sci., 9(4): 668, 2008

SUMMARY OF INVENTION

Technical Problem

Based on such background, the present invention aims to provide a novel DNA aptamer specifically binding to a molecular targeted medicine in purpose of measuring the blood concentration of a molecular targeted medicine.

Solution to Problem

The present inventors have carried out dedicated research to solve the above-mentioned problem, and a nucleotide sequence having a specific binding ability to a molecular targeted medicine has been specified by using SELEX methods. Then, a DNA having that specific sequence has been newly found to be able to function as a specific aptamer to a molecular targeted medicine, and thus, the present invention has been completed.

That is to say that, in one embodiment of the present invention:
(1) A DNA aptamer characterized by specifically binding to a molecular targeted medicine;
(2) A DNA aptamer characterized by specifically binding to a molecular targeted medicine, wherein the nucleotide sequence of the DNA aptamer comprises having a sequence comprising 1 to 3 nucleotide substitutions, deletions, or additions;
(3) The DNA aptamer according to the above-mentioned (1) or (2) specifically binding to a molecular targeted medicine having a nucleotide sequence of: 5'-$P_1$-X-$P_2$-3';
wherein X is a nucleotide sequence specifically binding to a molecular targeted medicine or is a sequence comprising 1 to 3 nucleotide substitutions, deletions, or additions, in a nucleotide sequence selected from the sequence, and $P_1$ and $P_2$ are a first and a second primer recognition sequence introduced for PCR amplification;
(4) The DNA aptamer according to the above-mentioned (3), wherein $P_1$ is a first primer recognition sequence shown in SEQ ID NO: 2 and $P_2$ is a second primer recognition sequence shown in SEQ ID NO: 3;
(5) The DNA aptamer according to any one of the above-mentioned (1) to (4) comprising at least one chemical modification selected from the group consisting of a chemical substitution at a sugar chain moiety, chemical substitution at a phosphate ester moiety, and chemical substitution at a nucleic acid base moiety;
(6) The DNA aptamer according to any one of the above-mentioned (1) to (5) having a fluorescent labelling at the 5' end or 3' end;
(7) The DNA aptamer according to the above-mentioned (6), wherein the fluorescent labelling is an organic fluorescence molecule with an emission wavelength from 421 nm to 712 nm comprising one or more kinds selected from green fluorescent protein (GFP), fluorescent protein, fluorescein isothiocyanate (FITC), 6-carboxyfluorescein-aminohexyl, fluorescein derivative, Alexa Fluor 350, Alexa Fluor 405, Alexa Fluor 488, Alexa Fluor 647, Alexa Fluor 750, rhodamine, 6-carboxytetramethylrhodamine, TAMRA (Registered Mark), Phycoerythrin (PE), phycocyanin (PC), PC5, PC7, Cy dyes, Cy3, Cy3.5, Cy5, Cy5.5, Cy7, TexasRed, allophycocyanin (APC), aminomethyl coumarin acetate (AMCA), Marina Blue, Cascade Blue, Cascade Yellow, Pacific Blue, SPRD, Tetramethylrhodamine isothiocyanate (TRITC), R110, mC1B, CellTracker dyes, CFSE, JC-1, PKH, DCFH-DA, DHR, FDA, Calcein AM, nitrobenzoxadiazole (NBD) group, dimethylamino sulphonyl benzooxadiazole group, acridine (Acd), dansyl (Dns), 7-dimethylaminocoumarin-4-acetic acid (DMACA), 5-((2-Aminoethyl)amino)naphthalene-1-sulfonic acid (EDANS), naphthalene, anthracene, and protoporphyrin 9;
(8) The DNA aptamer according to the above-mentioned (6), wherein the fluorescent labelling is a quantum dot;
(9) The DNA aptamer according to any one of the above-mentioned (1) to (8) having a fluorescent label at the 5' or 3' end, which is adsorbed onto a metal nanoparticle surface;
(10) The DNA aptamer according to the above-mentioned (9), wherein the metal used in the metal nanoparticle is gold, silver, copper, iron, or silicon; and
(11) The aptamer according to any one of the above-mentioned (1) to (10), wherein the molecular targeted medicine is Bevacizumab and the sequence specifically binding to the molecular targeted medicine is shown in SEQ ID NO: 1.

In another embodiment of the present invention, the present invention is related to the detection of a molecular targeted medicine using the above-mentioned DNA, and more particular, related to:
(12) A composition for detecting a molecular targeted medicine comprising the DNA aptamer according to any one of the above-mentioned (1) to (11);
(13) A kit for detecting a molecular targeted medicine comprising the DNA aptamer according to any one of the above-mentioned (1) to (11);
(14) A method for detecting a molecular targeted medicine comprising using the DNA aptamer according to any one of the above-mentioned (1) to (11);
(15) The method for detecting according to the above-mentioned (14), comprising contacting the DNA aptamer with a sample obtained from a living body selected from a group consisting of blood, blood serum, blood plasma, saliva, and sputum of a patient administered with a molecular targeted medicine, and detecting the presence of the molecular targeted medicine by observing the response caused by the binding of the sample and the DNA aptamer;
(16) The method for detecting according to the above-mentioned (15), wherein the response is a fluorescent response; and
(17) The method for detecting according to the above-mentioned (15), wherein the response is a Raman scattering response.

Advantageous Effects of the Invention

In accordance to the present invention, an efficient detection of a molecular targeted medicine is made possible by using a novel DNA aptamer which specifically binds to the molecular targeted medicine. In particular, the application to a kit comprising a DNA aptamer provided with a detection site such as fluorescent labelling and the like allows a convenient high-throughput detection and imaging with the molecular targeted medicine in blood collected from a living body as the subject of the measurement to be carried out. Furthermore, the application in a kit comprising a dispersion in which the DNA aptamer provided with a fluorescent labelling is adhered to metal nanoparticles and the like would allow a convenient high-throughput detection and imaging with the molecular targeted medicine in blood collected from the living body as the subject of the measurement to be carried out. Furthermore, by the detection of molecular targeted medicine in blood as such, the therapeutic effect of cancer could be improved.

Furthermore, as the consensus sequence in the DNA aptamer of the present invention is a relatively short region of only approximately 30 bases, it has an advantage that the time and trouble as well as cost for the production could be reduced, and the addition of a desired chemical modification and a further function depending on various uses, could be easily carried out.

DESCRIPTION OF EMBODIMENTS

Figure 1:
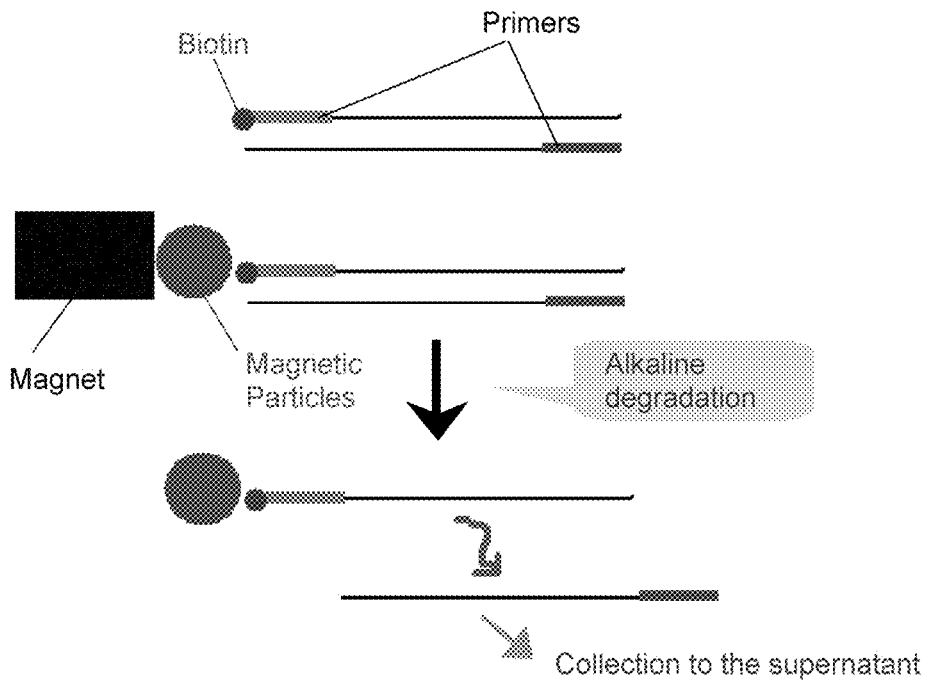
FIG. 1 is a schematic diagram showing the making of the double-stranded DNA into a single strand using magnetic particles.

Hereinafter, the embodiments of the present invention are described. Nonetheless, the scope of the present invention would not be restricted to these descriptions, and those other than the exemplifications mentioned below can be performed with appropriate modifications which are made without departing from the spirit of the present invention.

In the present specification, a molecular targeted medicine refers to an agent which among the agents used in the treatment of cancer, autoimmune diseases, organ transplantation, and the like, those that exert an effect in the treatment of diseases and suppression of rejection reaction, by attacking disease specific molecule, excessively expressed molecules, such as molecules and the like necessary for cell division of cancer, as a specific target, and suppressing their function. Examples of molecular targeted medicines of the present invention include antibody drugs used as anti-cancer agents or therapeutic drugs of autoimmune diseases such as mouse monoclonal IgG1 antibody, anti-human TNF-α antibody, mouse/human chimeric antibody, humanized anti-human IgE monoclonal antibody, anti-IL-5 monoclonal antibody, anti-RS viral antibody, anti-vascular endothelial growth factor (VEGF) antibody, PEGylated anti-human TNF-α antibody, humanized anti-CD20 receptor antibody, anti-CC chemokine receptor 4 humanized monoclonal antibody, humanized anti-CD5 antibody, anti-HER2 antibody, anti-CD52 antibody, anti-CD22 antibody, anti-CD20 antibody, human type anti-epidermal growth factor receptor (EGFR) monoclonal antibody, CTLA-4 (cytotoxic T lymphocyte-associated antigen 4, CD152) humanized antibody, and anti-VEGFR2 IgG1 antibody. Hereinbelow, cases when the molecular targeted medicine is Bevacizumab (Product Name: Avastin) is explained.

1. DNA Aptamer

The "DNA aptamer" in the present application refers to a single stranded oligo DNA that can specifically recognize the molecule or substance that would be the target, and the DNA aptamer according to the present invention is a single stranded oligo DNA having a function of specifically binding to Bevacizumab. In a typical embodiment, the DNA aptamer according to the present invention has a nucleotide sequence shown by SEQ ID NO: 1 as mentioned below. Note that the nucleotide sequence is described from the left to the right, from the direction of 5' end to the 3' end.

<SEQ ID NO: 1>
CCGTGTGGTGGGGGTTGGGGGTTGTCGTTCGCCG

The DNA aptamer of the present invention may be a sequence shown in the above-mentioned SEQ ID NO: 1 in which one or more of nucleotides are substituted, deleted, or added, as long as it has the function to specifically bind to Bevacizumab. Preferably, the nucleotides that are substituted, deleted, or added are 1 to 3 nucleotide(s), more preferably 1 or 2 nucleotide(s), and further preferably 1 nucleotide. Moreover, when such substitution, deletion, or addition of a nucleotide is present, the sequence of the DNA aptamer of the present invention can be a sequence which shows a homology of 90% or more, preferably 93% or more, or more preferably 96% or more, to the sequence shown in the above-mentioned SEQ ID NO: 1 (hereinafter, they can be referred to as "homologs"). Here, when used in the present specification, the term "homology" is used with a meaning generally recognized in the present technical field. The term typically refers to the number of nucleotides of the nucleic acid sequence of the subject matter matching to the nucleotides identical to the reference nucleic acid sequence, when examined by a sequence analysis program (for example, Karlin and Altschul, 1990, PNAS 87:2264-2268; Karlin and Altschul, 1993, PNAS 90:5873-5877) or a visual inspection.

When one or more nucleotides are substituted, the substitution can be carried out by a universal base. The term "universal base" refers to a meaning that is generally recognized in the present technical field. The term, in general, refers to a nucleotide base analogue that forms a base pair with each base of a standard DNA/RNA with hardly any difference and which can be recognized by an intracellular enzyme (for example, Loakes et al., 1997, J. Mol. Bio. 270: 426-435). Non-limiting examples of universal bases include, C-phenyl, C-naphthyl, and other aromatic derivatives, inosine, azole carbozamide, and nitroazole derivatives (3'-nitropyrole, 4-nitroindole, 5-nitroindole, 6-nitroindole, and the like) (Loakes, 2001, Nucleic Acids Res. 29: 2437).

Furthermore, there is no upper limit on the length of the DNA aptamer of the present invention as long as the DNA aptamer has the function to specifically bind to Bevacizumab. However, in view of the easiness of synthesis and problems of antigenicity and the like, the length of the DNA aptamer in the present embodiment, for example, as its upper limit, is 200 bases or less, preferably 150 bases or less, or more preferably 100 bases or less. When the number of the total bases is low, chemical synthesis and bulk production are easier, and there is a greater advantage in terms of cost. In addition, it is easily chemically modified, the safeness in the living body is high, and toxicity is low. The lower limit is provided as a number that is the same or more to the number of the bases in the above-mentioned SEQ ID NO: 1, i.e., 34 bases or more. A DNA aptamer is preferably a single-stranded DNA (ssDNA); however, even in a case where a partial double-stranded structure is formed by taking a hairpin loop type structure, the length of that DNA aptamer is calculated as a length of a single strand.

In a preferred embodiment, the DNA aptamer of the present invention may be of a nucleotide sequence consisting of the sequence of the above-mentioned SEQ ID NO: 1 and a primer recognition sequence attached thereto at each 5' and 3' end. In other words, in this case, the DNA aptamer has the following nucleotide sequence: 5'-$P_1$-X-$P_2$-3'; Wherein X is a nucleotide sequence shown in SEQ ID NO: 1 or is a sequence comprising 1 to 3 nucleotide substitutions, deletions, or additions, in this sequence. $P_1$ and $P_2$ are a first and a second primer recognition sequence introduced for PCR amplification. Preferably, $P_1$ is GCC TGT TGT GAG CCT CCT (SEQ ID NO: 2) and $P_2$ is CGC TTA TTC TTG TCT CCC (SEQ ID NO: 3).

The DNA aptamer of the present invention may be chemically modified for an increase of the stability in the living body. Unlimited examples of such chemical modifications include a chemical substitution at the sugar chain moiety (for example, 2'-O methylation); a chemical substitution at the phosphate ester moiety (for example, phosphorothioation, a chemical modification of an amino group, a lower alkyl amine group, or an acetyl group), and a chemical substitution at a base moiety. Similarly, an additional base could be provided at the 5' or 3' end. The length of such additional base is normally 5 bases or less. Additional bases may be a DNA or RNA; however, when DNA is used, the stability of the aptamer may increase. Sequences of such additional bases include sequences such as ug-3', uu-3', tg-3', tt-3', ggg-3', guuu-3', gttt-3', ttttt-3', and uuuuu-3', for example; however, they are not limited thereto.

Furthermore, for example, the DNA aptamer of the present invention can have a detection label linked to the 5' end or 3' end, for using it in the detection method of Bevacizumab or a kit used in the detection, as described hereinafter. As such detection label, fluorescent labelling is preferred; however, Raman scattering label, enzyme label, and infrared label may be used.

In fluorescent labelling, fluorescent label agent conventionally used in the present technical field could be used, for example, one or more kinds selected from the following is included: green fluorescent protein (GFP), fluorescent protein, fluorescein isothiocyanate (FITC), 6-carboxyfluorescein-aminohexyl, fluorescein derivative, Alexa Fluor 350, Alexa Fluor 405, Alexa Fluor 488, Alexa Fluor 647, Alexa Fluor 750, rhodamine, 6-carboxytetramethylrhodamine, TAMRA (Registered Mark), Phycoerythrin (PE), phycocyanin (PC), PC5, PC7, Cy dyes, Cy3, Cy3.5, Cy5, Cy5.5, Cy7, TexasRed, allophycocyanin (APC), aminomethyl coumarin acetate (AMCA), Marina Blue, Cascade Blue, Cascade Yellow, Pacific Blue, SPRD, Tetramethylrhodamine isothiocyanate (TRITC), R110, mC1B, CellTracker dyes, CFSE, JC-1, PKH, DCFH-DA, DHR, FDA, Calcein AM, nitrobenzoxadiazole (NBD) group, dimethylamino sulphonyl benzooxadiazole group, acridine (Acd), dansyl (Dns), 7-dimethylaminocoumarin-4-acetic acid (DMACA), 5-((2-Aminoethyl)amino)naphthalene-1-sulfonic acid (EDANS), naphthalene, anthracene, and protoporphyrin 9.

Preferably, for example, fluorophores that can be introduced by commercially available oligonucleotide solid phase synthesis services include such as 6-carboxytetramethylrhodamine (TAMRA (Trademark)), fluorescein isothiocyanate (FITC), 6-carboxyfluorescein-aminohexyl (FAM), cyanine fluorescent dyes (Cy3, Cy3.5, Cy5, and Cy5.5), and the like.

Moreover, a quencher that absorbs a fluorescence energy emitted from the fluorescent substance may be further bound adjacent to a fluorescent substance. In such embodiment, fluorescence is detected by the fluorescent substance and quencher being separated at the time of detection reaction. Examples of enzyme labelling include β-galactosidase, β-glucosidase, alkaliphosphatase, peroxidase, malate dehydrogenase, and the like. Moreover, as luminescent substrate, luminol, luminol derivative, luciferin, lucigenin, and the like may be used as a labelling agent.

For Raman scattering labelling, as a substituent having a binding ability with a metal surface which is located at the 5' end or 3' end, for example, of the above-mentioned fluorescent labelled aptamer, a group selected from a thiol (SH) group, an alkylamino group, an aromatic amino group, and a carboxyl group can be introduced without being particularly limited thereto, and then, for example, these can be adsorbed onto the surface of a gold nanoparticle for the detection of an enhanced Raman scattering emitted from the gold particles with adsorbed aptamers, thereby cell recognition is carried out. In this case, without particular being limited thereto, gold, silver, iron, quantum dots, and the like, can be used as metal nanoparticles.

2. Selection of DNA Aptamers

The DNA aptamer of the present invention can be selected and obtained by using a well-known in vitro selection method in the present technical field. As preferable examples of such method, Systematic Evolution of Ligands by Exponential enrichment: SELEX method is used. SELEX method includes selecting a nucleic acid ligand (aptamer) binding to a target substance and then repeatedly performing an exponential amplification by PCR for multiple times, and thereby a nucleic acid molecule (a single-stranded DNA, RNA) having an affinity to the target substance is obtained. Moreover, as its improved method, it is preferred to apply SELEX method such as disclosed in Guo, et al., Int. J. Mol. Sci., 9(4): 668, 2008. That is to say that SELEX method which prepares protein immobilized magnetic particles, mixes these with a nucleic acid library, extracts only nucleic acids having affinity to proteins on the magnetic particles, and performs PCR amplification.

As mentioned above, "in vitro selection method" is a method which selects aptamer molecules having an affinity to the target molecules and cells from a nucleic acid molecule pool containing random nucleotide sequences (i.e., DNA pool) and removes molecules which do not have an affinity. Furthermore, this is a method that allows the enrichment of an aptamer molecule having a strong binding ability by repeating the cycle which includes only amplifying the selected aptamer molecules using PCR methods and the like and performing the selection by affinity.

Specifically, first of all, a single-stranded nucleic acid molecule comprising a random nucleotide sequence (base sequence) region of 20 to 300 bases, preferably, 30 to 150 bases, or more preferably 30 to 100 bases, for example, an oligo DNA, is prepared. For an oligo DNA to allow PCR (Polymerase Chain Reaction) amplification, using those having base sequences that serve as primers at both ends is preferable. The primer recognition sequence moiety may have an appropriate restriction enzyme site so that the primer moiety could be excised by a restriction enzyme after a PCR amplification. The length of the primer recognition sequence moiety to be used is not particularly limited; however, it is approximately 20 to 50, preferably 20 to 30 bases. Moreover, for allowing the separation of a single-stranded DNA after PCR amplification by electrophoresis and the like, labelling such as with radioactive labelling and fluorescent labelling at the 5' end can be carried out.

Next, nucleic acid molecules having the random nucleotide sequence obtained as above (library pool) can be mixed with a target protein immobilized onto magnetic microparticles at an appropriate concentration ratio, and this is incubated under an appropriate condition. After incubation, this is allowed to stand still on a magnetic stand, and the nucleic acid molecule-target protein complex and free nucleic acid molecules are separated. Then, the supernatant portion of the separated solution is removed and PCR reaction is carried out by using the obtained nucleic acid molecule-target protein complex to perform the amplification of the target protein binding nucleic acid sequence. Subsequently, a nucleic acid molecule which forms a complex with the target protein is made into a single strand according to the well-known methods in the present technical field. Such means include the separation utilizing the binding of streptavidin-immobilized magnetic particles with biotin, for example. Due to this, ssDNA having a target protein binding ability can be separated from an amplified nucleic acid double-stranded chain, and moreover, unnecessary coexisting substance contained in the PCR reaction solution such as DNA polymerase could be removed. After this, a similar operation is carried out using the collected ssDNA as a library pool.

A series of operations from mixing with the above-mentioned nucleic acid molecule and the target protein, separating the nucleic acid molecule bound with the target protein, PCR amplification, and using the amplified nucleic acid molecule once again in the binding with the target protein is carried out for a couple of rounds. By repeating the rounds, a nucleic acid molecule which more specifically binds with a target cell can be selected. The sequence analysis of the obtained nucleic acid molecule can be carried out by the well-known methods in the present technical field.

3. Compositions for Detecting Bevacizumab, Methods for Detection, and Kit

As mentioned above, the DNA aptamer of the present invention has a function specifically binding to Bevacizumab, and thus, it can be preferably used in the detection of the blood concentration of Bevacizumab.

Specifically, the composition for detection comprising a DNA aptamer of the present invention is contacted with samples obtained from a living body selected from a group consisting of blood, blood serum, blood plasma, saliva, and sputum. Then, the detection of the presence of Bevacizumab is made by observing the response (presence of the signal) caused by the binding of the sample with a DNA aptamer. "Samples obtained from a living body" are obtained from animals, preferably from human; however, as long as the samples are samples or secreted body fluid that can be assured to be obtained at minimal invasion or in vitro cell culture solution component samples and the like, the form is not particularly restricted. Moreover, the "response" for detecting the presence of Bevacizumab is preferably a fluorescent response or a Raman scattering response, and as mentioned above, it is preferred to link the fluorescent labelling agent such as TAMRA (Trade Mark) and FITC at the 5' or 3' end of the DNA aptamer in a fluorescence response. Furthermore, in the Raman scattering response, it is preferred that Cy3.5 (Trade Mark), TAMRA (Trade Mark), fluorescent labelling agent such as FITC are linked to the 5' end or 3' end of the DNA aptamer, and a group selected from the above-mentioned thiol (SH) group, alkylamino group, aromatic amino group, and carboxyl group are introduced, and for example, these are preferably adsorbed onto the surface of a gold nanoparticle.

The composition for detecting Bevacizumab of the present invention can be provided as a kit comprising a DNA aptamer enhancing the convenience or portability. In the kit, the DNA aptamer can be provided in an embodiment of an aqueous solution in which the DNA aptamer is generally dissolved at an appropriate concentration or in an embodiment of a DNA array in which the DNA aptamer is immobilized on a solid phase support. For example, biotin can be bound to the end of the DNA aptamer to form a complex, streptavidin can be immobilized on the surface of a solid phase support, and the DNA aptamer can be immobilized on the surface of the solid phase support by the interaction of biotin and streptavidin. The kit may appropriately contain other reagents and the like as necessary, and for example, additives such as solubilizing agents, pH adjusting agents, buffer agents, and tonicity agents can be used, and the formulation amount can appropriately be selected by those skilled in the art.

When the molecular targeted medicine of the present invention that is subjected for measurement are those as mentioned above and are those other than Bevacizumab, the present invention can be performed as mentioned above.

The pharmaceutical composition of the present invention, for example, can be administered to mammals (e.g., human, rat, mouse, rabbit, sheep, pig, cow, cat, dog, monkey, and the like).

EXAMPLES

Hereinafter, the present invention will be further described in detail with reference to the Examples, but the present invention is not limited thereto.

Example 1: Selection of the Aptamers

The selection of aptamers specifically binding to Bevacizumab which is a lung cancer molecular targeted medicine from DNA pools having random sequences has been carried out using SELEX method. Each of the steps in the SELEX method is as follows:

1) Preparation of a DNA pool (Preparation of solution of a group of DNA aptamer candidates)

2) Preparation and Mixture of a target substance-Bevacizumab immobilized magnetic particles 3) Separation of the target binding DNA and non-binding DNA 4) Replication of the target binding DNA (a step of amplifying a DNA aptamer bound with the target substance)

5) Purification of target binding DNA (a step of purifying the amplified DNA aptamer into a single stranded DNA)

6) Cloning of target binding nucleic acid (pre-treatment of the sequence analysis of the obtained DNA aptamer)

7) Performing 6 rounds of these steps 1) to 6)
8) Sequence analysis of the target binding nucleic acid (analysis of nucleotide sequence of the DNA aptamer using a sequencer)

A further detailed experimental procedure is given as below. For DNA pools, an oligo DNA of a total length of 70 bases of the below-mentioned sequence in which 34 bases are the random sequence portion (N) was used. DNA pool: Random 34 (manufactured by TSUKUBA OLIGO SERVICE CO., LTD.)

```
-SEQUENCE:
5'-GCC TGT TGT GAG CCT CCT(N34)CGC T TA TTC TTG
TCT CCC-3'
```

Length: 70 bases (random sequence corresponds to the 34 bases in the middle)
Molecular weight: 21391.3 g/mol
Molar absorption coefficient: 630475 L/mol·cm
The sequences of both ends of the random sequence are recognized by primers in the subsequent PCR, and they are sequences that allow amplification.

The immobilization of Bevacizumab to the surface of the magnetic particles was carried out in accordance to the instruction manual attached to AVASTIN. As for the magnetic particles, Protein A Magnetic Beads (product 88845) manufactured by Thermo Scientific were used.

Examples of SELEX Using Magnetic Particles

Seventeen μL of Bevacizumab immobilized magnetic particles was measured, and then, washed well with phosphate buffer (pH 7.4, Ca, Mg free, 2 mM EDTA, 0.1% HSA). To this, 20 μL of a DNA library prepared at 10 μM was added. After being allowed to stand still at room temperature for 30 minutes, magnetic particles were collected using a magnetic stand, washed with phosphate buffer (2 mM ETDA, 0.1% BSA), and finally substituted with 20 μL of TE buffer. This was allowed to stand still for 10 minutes on a heat block at 95° C. for 10 minutes, and the DNA adsorbed on Bevacizumab on magnetic particles was detached. The recovered DNA library was amplified by using PCR and the target DNA sequence was collected.

Streptavidin was added to the purified DNA to be adsorbed to magnetic particles and the supernatant was removed once the magnetic particles were recovered using magnets, and then a single-stranded DNA which did not bind to the magnetic particles was collected in the supernatant by alkaline buffer degradation (FIG. 1). Subsequently, alkaline buffer was substituted with a PBS buffer and the target single-stranded DNA binding to a magnetic particle was collected. This procedure was considered as one round, and this operation was carried out 8 times.

Once the 6 rounds were completed, PCR amplification was performed using a non-biotinylated 18-bases primer, and the PCR product was analyzed using a sequencer.

Example 2: Staining of Bevacizumab Using a Fluorescent Labelled DNA Aptamer

Figure 2:
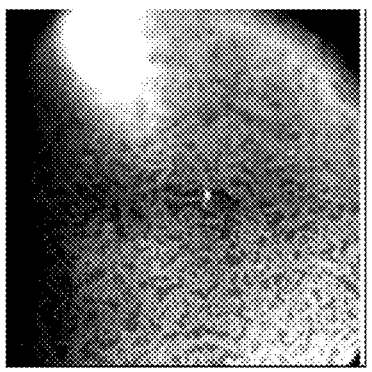
FIG. 2 is a real image of Bevacizumab adsorbed magnetic particles with a DNA aptamer of SEQ ID NO: 1.
Figure 3:
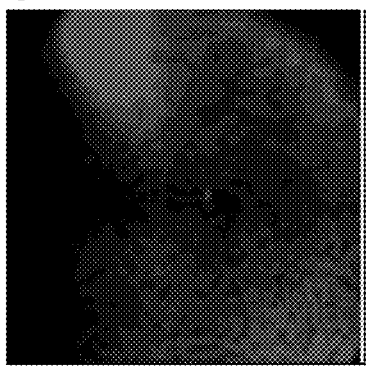
FIG. 3 is fluorescent imaging of Bevacizumab adsorbed magnetic particles with a DNA aptamer of SEQ ID NO: 1.

Bevacizumab immobilized on Protein A Magnetic Beads was placed in a 1.5 mL centrifuge tube. To these, a modification with Cy3.5 (Trademark) at the 5' end of DNA aptamer consisting of a nucleotide sequence having an affinity to the Bevacizumab found by sequencing analysis was carried out, and 20 μl of this DNA was prepared into a aptamer solution to be 100 μM with ultrapure water, which was dispersedly added to a 1.5 mL centrifuge tube having a 1 mL phosphate buffer solution. This was allowed to stand still in an incubator at 37° C. for 1 hour. After this, the cells were washed 3 times with PBS, and then they were observed under the inverted fluorescence microscope IX71 manufactured by Olympus at a condition where 2 mL of PBS was added. The results shown by the DNA aptamer having SEQ ID NO: 1 is each shown in FIG. 2 and FIG. 3. Accordingly, by this, it was revealed that these fluorescent labelled DNA aptamers specifically bind to Bevacizumab on the magnetic particles and a well fluorescence imaging image for Bevacizumab were obtained.

Example 3 Measurement of the Binding Constant on Bevacizumab

Two hundred μL of Bevacizumab (100 mg/4 mL) solution was added to a cup to which a sensor chip is attached for use in quartz crystal microbalance (AFFINIXQ8 ULVAC, Inc.). Then, this was allowed to stand still at 37° C. for 2 hours, and after that the Bevacizumab solution was carefully removed using a pipette, washed 3 times with 200 μL of phosphate buffer (Gibco DPBS), and finally placed to a cup of 200 μL phosphate buffer solution to be loaded on the device. Once the sensor cup was loaded, a mixer was fixed on this and the sensor switch was turned on while stirring. When the pressure variation of the quartz crystal units was controlled, an aptamer was added to each of sensor cups 1 to 4 to a concentration of 1.48 μM, 1.98 μM, 2.32 μM, and 2.91 μM, respectively, and they were measured until the adsorption curve was stabilized.

Figure 4:
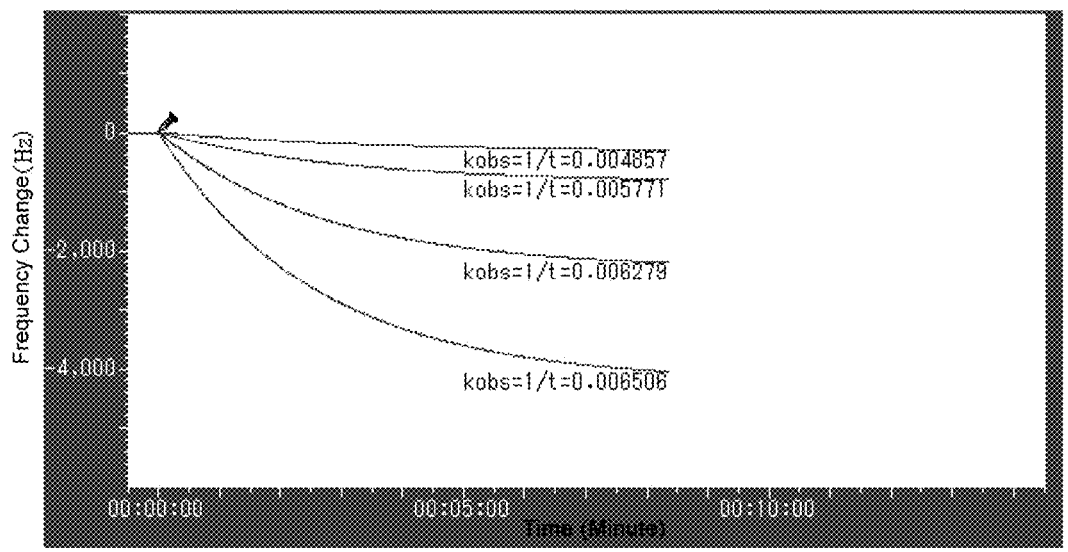
FIG. 4 is an image showing the adsorption properties of the aptamer molecules on the Bevacizumab immobilized surface.
Figure 5:
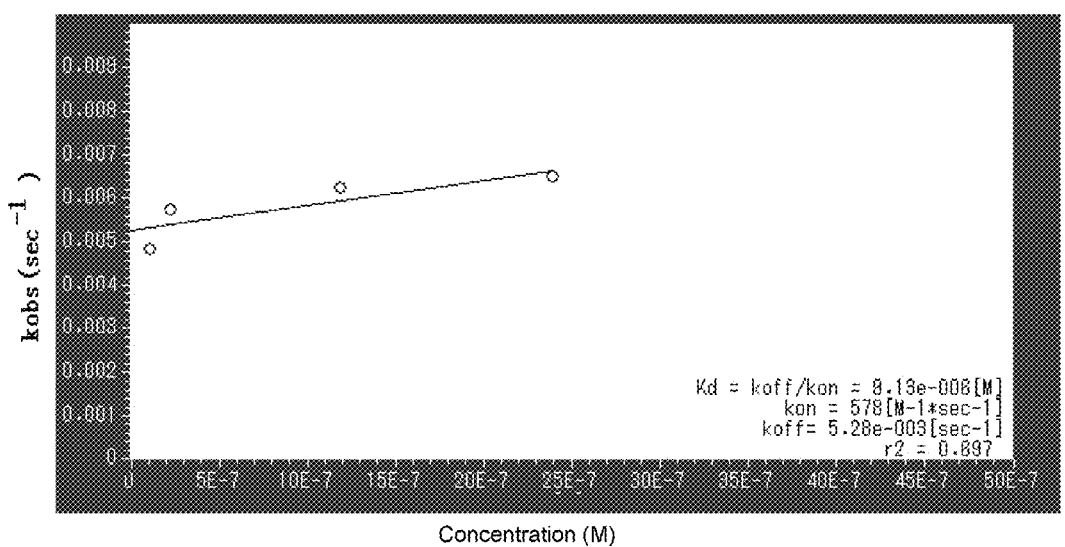
FIG. 5 is an image showing a disassociation constant obtained from the adsorption properties of the aptamer molecules on the Bevacizumab immobilized surface using velocity analysis.

FIG. 4 and FIG. 5 each shows the adsorption properties of the aptamer molecules on the Bevacizumab immobilized surface and a dissociation constant calculated by speed analysis method. The dissociation constant of the present aptamer on Bevacizumab is approximately $9.1 \times 10^{-6}$M, and it is understood that it strongly binds to Bevacizumab.

INDUSTRIAL APPLICABILITY

The aptamer of the present invention is extremely useful for such as the measurement of blood concentration of molecular targeted medicine and the application in the medical field is expected.

The invention claimed is:

1. A DNA aptamer having a nucleotide sequence of SEQ ID NO:1 specifically binding to Bevacizumab.

2. The DNA aptamer according to claim 1 comprising at least one chemical modification selected from the group consisting of a chemical substitution at a sugar chain moiety, chemical substitution at a phosphate ester moiety, and chemical substitution at a nucleic acid base moiety.

3. The DNA aptamer according to claim 2 having a fluorescent labelling at the 5' end or 3' end.

4. The DNA aptamer according to claim 3, wherein the fluorescent labelling is one or more kinds selected from green fluorescent protein (GFP), fluorescent protein, fluorescein isothiocyanate (FITC), 6-carboxyfluorescein-aminohexyl, fluorescein derivative, Alexa Fluor 350, Alexa Fluor 405, Alexa Fluor 488, Alexa Fluor 647, Alexa Fluor 750, rhodamine, 6-carboxytetramethylrhodamine, TAMRA (Registered Mark), Phycoerythrin (PE), phycocyanin (PC), PC5, PC7, Cy dyes, Cy3, Cy3.5, Cy5, Cy5.5, Cy7, TexasRed, allophycocyanin (APC), aminomethyl coumarin acetate (AMCA), Marina Blue, Cascade Blue, Cascade Yellow, Pacific Blue, SPRD, Tetramethylrhodamine isothiocyanate (TRITC), R110, mC1B, CellTracker dyes, CFSE, JC-1, PKH, DCFH-DA, DHR, FDA, Calcein AM, nitrobenzoxadiazole (NBD) group, dimethylamino sulphonyl benzooxadiazole group, acridine (Acd), dansyl (Dns), 7-dimethylaminocoumarin-4-acetic acid (DMACA), 5-((2-Aminoethyl)amino)naphthalene-1-sulfonic acid (EDANS), naphthalene, anthracene, and protoporphyrin 9.

5. The DNA aptamer according to claim 3, wherein the fluorescent labelling is a quantum dot.

6. The DNA aptamer according to claim 5 having a fluorescent label at the 5' or 3' end, which is adsorbed onto a metal nanoparticle surface.

7. The DNA aptamer according to claim 6, wherein the metal used in the metal nanoparticle is gold, silver, copper, iron, or silicon.

8. A composition for detecting a molecular targeted medicine comprising the DNA aptamer according to claim 1.

9. A kit for detecting a molecular targeted medicine comprising the DNA aptamer according to claim 1.

10. A method for detecting Bevacizumab, comprising contacting the DNA aptamer having a nucleotide sequence of SEQ ID NO:1 with a sample obtained from a living body selected from a group consisting of blood, blood serum, blood plasma, saliva, and sputum, and detecting the presence of the molecular targeted medicine by observing the response caused by the binding of the sample and the DNA aptamer.

11. The method for detecting according to claim 10, wherein the response is a fluorescent response.

12. The method for detecting according to claim 10, wherein the response is a Raman scattering response.

* * * * *

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial sequence
<220> FEATURE:
```

-continued

```
<223> OTHER INFORMATION: aptamer for bevacizumab

<400> SEQUENCE: 1
ccgtgtggtg ggggttgggg gttgtcgttc gccg                                    34

<210> SEQ ID NO 2
<211> LENGTH: 18
<212> TYPE: DNA
<213> ORGANISM: Artificial Sequence
<220> FEATURE:
<223> OTHER INFORMATION: Primer binding to site P1

<400> SEQUENCE: 2
gcctgttgtg agcctcct                                                      18

<210> SEQ ID NO 3
<211> LENGTH: 18
<212> TYPE: DNA
<213> ORGANISM: Artificial sequence
<220> FEATURE:
<223> OTHER INFORMATION: Primer binding to site P2

<400> SEQUENCE: 3
cgcttattct tgtctccc                                                      18

<210> SEQ ID NO 4
<211> LENGTH: 70
<212> TYPE: DNA
<213> ORGANISM: Artificial Sequence
<220> FEATURE:
<223> OTHER INFORMATION: DNA Pool random 34
<220> FEATURE:
<221> NAME/KEY: misc_feature
<222> LOCATION: (19)..(52)
<223> OTHER INFORMATION: n is a, c, g, or t

<400> SEQUENCE: 4
gcctgttgtg agcctcctnn nnnnnnnnnn nnnnnnnnnn nnnnnnnnnn nncgcttatt        60
cttgtctccc                                                               70
```